(12) United States Patent
Kiridena et al.

(10) Patent No.: US 8,618,226 B2
(45) Date of Patent: Dec. 31, 2013

(54) METHOD FOR QUANTITATIVE ANALYSIS OF STYRENE MICROBLOCK CONTENT

(75) Inventors: Waruna Chethiya Bandara Kiridena, Copley, OH (US); Mindaugas Rackaitis, Massillon, OH (US); Terrence Eugene Hogan, Uniontown, OH (US); Dennis R. Brumbaugh, North Canton, OH (US); William L. Hergenrother, Akron, OH (US)

(73) Assignee: Bridgestone Corporation, Tokyo (JP)

( * ) Notice: Subject to any disclaimer, the term of this patent is extended or adjusted under 35 U.S.C. 154(b) by 0 days.

(21) Appl. No.: 13/476,387

(22) Filed: May 21, 2012

(65) Prior Publication Data

US 2012/0296054 A1    Nov. 22, 2012

Related U.S. Application Data

(60) Provisional application No. 61/487,756, filed on May 19, 2011.

(51) Int. Cl.
| | |
|---|---|
| *G01N 3/44* | (2006.01) |
| *C08F 6/00* | (2006.01) |
| *G01N 1/22* | (2006.01) |
| *C08F 236/10* | (2006.01) |

(52) U.S. Cl.
USPC ............... 526/60; 526/340; 528/481; 436/85; 73/23.41; 73/863.12

(58) Field of Classification Search
USPC ........... 436/85; 526/60, 340; 73/23.38, 23.41, 73/863.12; 528/481
See application file for complete search history.

(56) References Cited

U.S. PATENT DOCUMENTS

| | | | |
|---|---|---|---|
| 4,159,894 A * | 7/1979 | Hu | ..................... 436/60 |
| 5,528,036 A | 6/1996 | Achter et al. | |
| 6,072,576 A | 6/2000 | McDonald et al. | |
| 6,223,133 B1 | 4/2001 | Brown | |
| 6,294,388 B1 | 9/2001 | Petro | |
| 6,507,401 B1 | 1/2003 | Turner et al. | |
| 6,608,678 B1 | 8/2003 | Potyrailo et al. | |
| 6,904,785 B1 | 6/2005 | Cassisa et al. | |
| 7,307,257 B2 | 12/2007 | Long et al. | |
| 7,505,129 B2 | 3/2009 | Marrow et al. | |

OTHER PUBLICATIONS

N. Dimov, et al, "Post-Column Gas Chromatography for Improved Analysis of Copolymers," Chromatographia, vol. 17, No. 7, Jul. 1983.*

(Continued)

*Primary Examiner* — Fred M Teskin
(74) *Attorney, Agent, or Firm* — Meredith E. Hooker; Arthur M. Reginelli

(57) ABSTRACT

A method for determining the styrene microblock content of a copolymer sample, the method comprising: (i) pyrolyzing the copolymer sample to form polymer fragments of the polymer sample; (ii) analyzing the fragments to determine the relative amounts of styrene monomer fragments, styrene dimer fragments, and styrene trimer fragments, where the relative amounts of the fragments include the amount of any given fragment relative to the total of the monomer fragments, dimer fragments, and trimer fragments; and (iii) using the relative amounts of the styrene monomer fragments, styrene dimer fragments, and styrene trimer fragments to predict the polystyrene microblock content from a mathematical model that is based upon the relative styrene monomer fragments, relative styrene dimer fragments, relative styrene trimer fragments, and microblock content of a copolymer having known microblock content.

13 Claims, 1 Drawing Sheet

(56) References Cited

OTHER PUBLICATIONS

M. Blazso, et al, "Pyrolysis-gas chromatography of styrene-acrylonitrile copolymers: Calculation of kinetic parameters and sequence distribution," J. of Analytical and Applied Pyrolysis, vol. 2, Issue 3, Nov. 1980, 177-185.*

Quantification of End Groups in Polystyrenes by Pyrolysis-Gas Chromatography, Y. Ito, H. Ohtani, S. Ueda, Y. Nakashima, S. Tsuge, Journal of Polymer Science: Part A: Polymer Chemistry, vol. 32, pp. 383-388 (1994).

Characterization of Stereoregular Polystyrenes by Pyrolysis-Gas Chromatography, T. Nonbe, H. Ohtani, T. Usanni, T. Mori, H. Fukumori, Y. Hirata, S. Tsuge., Journal of Applied Pyrolysis, 33, pp. 121-138, (1995).

R. P. Quirk, H.L. Hsieh, Anionic Polymerization, Chapter 7, Marcel Dekker, Inc., New York, 1996; pp. 155-171.

"Determination of Sequence Distribution in Styrene-Butadiene Copolymer i. 1 H-NMR Study of Styrene Oligomers", Tanaka et al., Rubber Chemistry and Technology vol. 54; pp. 685-691.

* cited by examiner

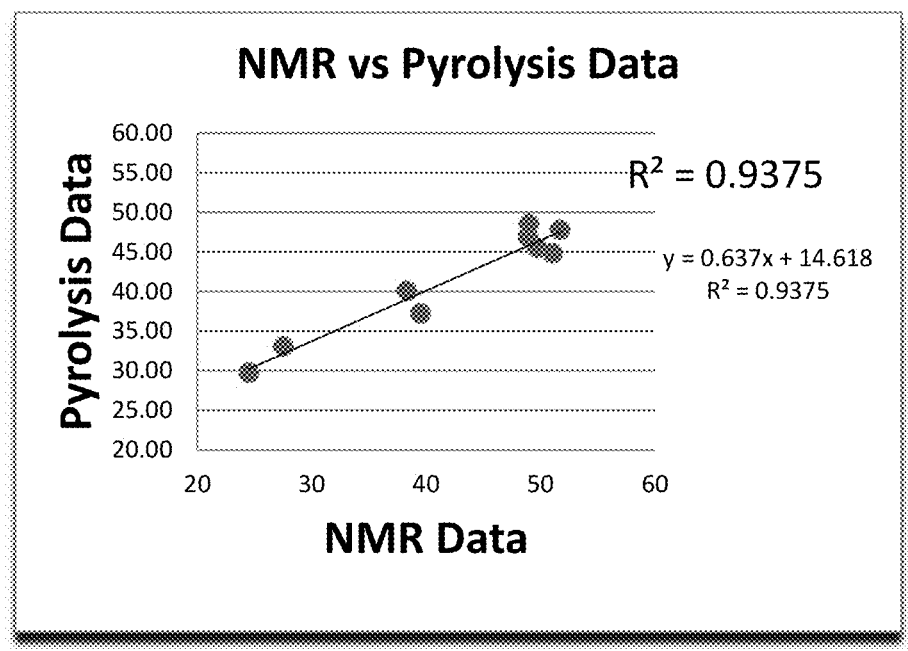

METHOD FOR QUANTITATIVE ANALYSIS OF STYRENE MICROBLOCK CONTENT

This application claims the benefit of U.S. Provisional Application Ser. No. 61/487,756, filed on May 19, 2011, which has been incorporated herein by reference.

FIELD OF THE INVENTION

Embodiments of the present invention are directed toward methods for quantitatively determining the styrene microblock content of copolymers such as styrene-diene copolymers. In specific embodiments, the analytical technique includes pyrolysis of the copolymer, gas chromatography separation of the pyrolyzed segments, and flame ionization detection.

BACKGROUND OF THE INVENTION

Random copolymers of vinyl aromatic and conjugated diene monomer (e.g., poly(styrene-co-butadiene)), are industrially useful. For example, these random copolymers are often used in the manufacture of tire components such as tire treads.

Those skilled in the art appreciate that these copolymers are not entirely random and that blocks of vinyl aromatic mer units, such as styrene mer units, exist in the polymer chain. And, it is believed that the presence of these blocks, particularly those of a smaller size, can be advantageous to the performance of the polymer. Accordingly, synthetic techniques have been developed to control the presence and size of these vinyl aromatic blocks.

The vinyl aromatic blocks that are believed to be advantageous are referred to as microblocks. These microblocks generally include from about 2 to about 12 repeating vinyl aromatic mer units with the preferred range generally including from about 3 to about 10 repeating mer units. The amount of these microblocks within a given polymer can be expressed as a weight average based upon the weight of all styrene within the copolymer. For example, a copolymer having 10 percent microblock content is a copolymer wherein 10 weight percent of the styrene mer units of the copolymer are located within microblocks. The balance of the styrene mer units may include completely random styrene mer units or styrene mer units located in blocks that are larger than microblocks.

Nuclear magnetic resonance (NMR) has been employed to quantitatively determine the styrene microblock content of copolymers. See, for example, *Determination of Sequence Distribution in Styrene-Butadiene Copolymer i. $^1$H-NMR Study of Styrene Oligomers*, Tanaka, et al. 685 RUBBER CHEMISTRY AND TECHNOLOGY VOL. 54. This method has advantageously provided quantitative analysis of styrene microblock content with high levels of accuracy and reproducibility. While this is a useful technique, especially within research and development settings, the technique is not as useful for manufacturing quality control (QC) because QC labs are often not equipped with personnel and/or equipment needed to perform NMR analysis. There is, however, a need for QC analysis of styrene microblock content that has a high degree of quantitative precision and reproducibility.

SUMMARY OF THE INVENTION

One or more embodiments of the present invention provides a method for determining the styrene microblock content of a copolymer sample, the method comprising: (i) pyrolyzing the copolymer sample to form polymer fragments of the polymer sample; (ii) analyzing the fragments to determine the relative amounts of styrene monomer fragments, styrene dimer fragments, and styrene trimer fragments, where the relative amounts of the fragments include the amount of any given fragment relative to the total of the monomer fragments, dimer fragments, and trimer fragments; and (iii) using the relative amounts of the styrene monomer fragments, styrene dimer fragments, and styrene trimer fragments to predict the polystyrene microblock content from a mathematical model that is based upon the relative styrene monomer fragments, relative styrene dimer fragments, relative styrene trimer fragments, and microblock content of a copolymer having known microblock content.

Still other embodiments of the present invention provide a method for synthesizing a copolymer, the method comprising the steps of: (i) polymerizing vinyl aromatic monomer and conjugated diene monomer to form a copolymer; (ii) obtaining a sample of the copolymer prepared by said step of polymerizing; (iii) determining the polystyrene microblock content the sample by (a) pyrolyzing the copolymer sample to form polymer fragments of the polymer sample; (b) analyzing the fragments to determine the relative amounts of styrene monomer fragments, styrene dimer fragments, and styrene trimer fragments, where the relative amounts of the fragments include the amount of any given fragment relative to the total of the monomer fragments, dimer fragments, and trimer fragments; and (c) using the relative amounts of the styrene monomer fragments, styrene dimer fragments, and styrene trimer fragments to predict the polystyrene microblock content from a mathematical model that is based upon the relative styrene monomer fragments, relative styrene dimer fragments, relative styrene trimer fragments, and microblock content of a copolymer having known microblock content; and (iv) optionally adjusting said step of polymerizing to adjust the microblock content of the copolymer.

FIGURES

The drawing is a graphical plot showing the cross correlation of the microblock content determined by practice of one or more embodiments of the invention versus microblock content determined by NMR.

DETAILED DESCRIPTION OF ILLUSTRATIVE EMBODIMENTS

Embodiments of the present invention are based, at least in part, on the discovery of an analytical technique for determining the styrene microblock content of copolymers by making predictions based upon the relative content of fragments that result from pyrolysis of the copolymer. For example, the method can include predicting the styrene microblock content of the copolymer based upon the relative amounts of styrene monomer fragments, styrene dimer fragments, and styrene trimer fragments resulting from pyrolysis of the copolymer. It has unexpectedly been observed that a relationship exists between the relative amounts of fragments resulting from pyrolysis (e.g. styrene monomer fragments, styrene dimer fragments, and styrene trimer fragments), and it has been observed that this relationship advantageously provides the ability to analyze microblock content with technologically useful accuracy. Thus, while the prior art may have contemplated analytical techniques that include pyrolysis of a copolymer sample to predict microblock content based upon individual fragments from pyrolysis, such as trimer fragments, the prior art did not appreciate that a linear relationship exists between the microblock content and the relative content of three or more fragments that result from pyrolysis. Moreover, especially in those embodiments where relative monomer content, dimer content, and trimer content are employed in the analytical technique, the prior art did not recognize the accuracy and repeatability that could be obtained by relying on data from these fragments. Additionally, it has been further discovered that by determining total styrene content of the copolymers in question and using this data in conjunction with the relative amounts of monomer, dimer and trimer resulting from pyrolysis, the accuracy of the analytical technique can advantageously be improved.

Polymer Sample

In one or more embodiments, the polymer samples that can be analyzed by practice of the present invention include random copolymers of vinyl aromatic monomer and diene monomer. Examples of vinyl aromatic monomers include styrene, α-methylstyrene, p-methylstyrene, and vinyl naphthalene. Examples of diene monomers include 1,3-butadiene, isoprene, 1,3-pentadiene, 2,3-dimethyl-1,3-butadiene, and 1,3-hexadiene. The polymer samples may be referred to as copolymers or random copolymer. In one or more embodiments, the polymers may be referred to as poly(vinyl aromatic-co-diene) copolymers. Specific examples include poly(styrene-co-butadiene) copolymers, poly(styrene-co-isoprene) copolymers, poly(styrene-co-isoprene-co-butadiene) and copolymers.

In one or more embodiments, the copolymers analyzed in the practice of this invention are devoid of or substantially devoid of macroblock polystyrene. For purposes of this specification, macroblock refers to blocks of styrene including more than 30 styrene repeat units within a block. Likewise, the copolymers employed in building a mathematical model, which is described below, are devoid or substantially devoid of macroblock polystyrene. For purposes of this specification, substantially devoid refers to that amount of macroblock polystyrene or less that will not have an appreciable impact on the methods described; e.g. will not have an appreciable impact on the accuracy of the method.

In one or more embodiment, the copolymer analyzed in the practice of this invention have a number average molecular weight of at least 5 kg/mole, in other embodiments at least 15 kg/mole, in other embodiments at least 35 kg/mole, and in other embodiments at least 50 kg/mole. In these or other embodiments, the copolymer have a number average molecular weight of from about 5 kg/mole to about 500 kg/mole, in other embodiments from about 20 to about 400 kg/mole, and in other embodiments from about 50 to about 250 kg/mole.

Practice of the present invention is specifically directed toward determining the vinyl aromatic microblock content of copolymers. Styrene is a widely-employed vinyl aromatic monomer and therefore practice of the present invention is particularly useful for determining the styrene microblock content of copolymers. For ease of description, the written description and claims may be defined in terms of styrene microblock content, although those skilled in the art will appreciate that these techniques, as well as the scope of the invention, are equally applicable to determining the microblock content deriving from any vinyl aromatic monomer. For purposes of this description, the styrene microblock content may be referred to as microblock polystyrene content or simply as microblock content.

In one or more embodiments, practice of the present invention is not limited to the fragments that are analyzed. As those skilled in the art appreciate, the pyrolysis of random copolymers of vinyl aromatic monomer and diene monomer can yield numerous fragments such as ethane, 1-propene, 2-methylpropene, 2-butene, 1,3-butadiene, 1,3-pentadiene, 1,4-pentadiene, 1,4-hexadiene, cyclohexene, 1,3,5-hexatriene, 1,3,6-octatriene, octadiene, 2,6-octadiene, benzene, ethenylcyclohexane, 4-ethenylcyclohex-1-ene, 1,2-demethylenecyclohexane, 1,3,5-octatriene, toluene, 2,3-dimethyl-1,3-cyclohexadiene, ethylbenzene, 1,4-dimethylbenzene, propylbenzene, styrene, 1-propenylbenzene, 4-methylenetricyclodecane, 1-vinyl-4-methylbenzene, 1,5-diethenyl-3-methyl-2-methylenecyclohexane, 1,4-divinyl-octahydropentalene, spiro(2.9)dodeca-4,8-diene, 2-propenylbenzene, spiro(2.9)dodeca-5,9-diene, 2,6-diethenyl-cis-cyclooctene, 1-methylenebutylbenzene, 2,6-diethenyl-cis-cyclooctene isomer, spiro(2.9)dodeca-4,8-diene isomer, 1,4,8-dodecatriene, 1,3-divinylbenzene, 1-phenyl-1,3-heptadiene, 4-methyl-2,6-(1,1-dimethylethyl) phenol (BHT), diphenylmethane, 1,1'-(1,3-propandiyl)bisbenzene, (3-phenylbul-3-enyebenzene or styrene dimmer, 1,1'-cyclopropylidenebisbenzene, 1,1'-(1,2-ethenediyebis-benzene, and 1,1'-(1-butene-1,4-diyebisbenzene. See ANALYTICAL PYROLYSIS OF SYNTHETIC ORGANIC POLYMERS by Moldoveanu, 2005, page 259.

In one or more embodiments, practice of the present invention, including the building of a mathematical model and the analysis of copolymer samples, contemplates using any of the various fragments. In one or more embodiments, the techniques described herein include analyzing at least three fragments, which number is believed to provide statistically sound accuracy and repeatability to the methods. Those skilled in the art appreciate that, once armed with the teachings of this invention, a preference may exist to analyze those peaks that provide the greatest, or generally greater, response to detection; e.g. yield the greatest area in a detection curve.

In one or more embodiments, practice of the present invention includes analyzing fragments of styrene monomer, fragments of styrene dimer, and fragments of styrene trimer. For ease of description, these fragments may be referred to simply as styrene monomer fragments, styrene dimer fragments, and styrene trimer fragments, or simply monomer fragments, dimer fragments, and trimer fragments, respectively. As those skilled in the art appreciate, the styrene monomer fragments will have a molecular weight of about 104 g/mole, styrene dimer fragments will have a molecular weight of about 208 g/mole, and styrene trimer fragments will have a molecular weight of about 312 g/mole. It is believed that these fragments bear a particularly advantageous relationship to microblock. Accordingly, for ease of describing the invention, the illustrative embodiments described herein are described with reference to styrene monomer fragments, styrene dimer fragments, and styrene trimer fragments, with the understanding that those skilled in the art will be able to extend these teachings to the use of other fragments without undue experimentation or calculation.

Analytical Method

The method of one or more embodiments of the present invention includes (i) pyrolyzing the polymer sample to form polymer fragments, (ii) analyzing the polymer fragments, and (iii) applying the data obtained from the analysis to a mathematical model to thereby predict the microblock content of the polymer sample.

In one or more embodiments, the step of pyrolyzing is conducted under conditions to maximize formation of the trimer. As those skilled in the art appreciate, the pyrolysis conditions, such as time and temperature, can be manipulated to achieve different results. And, those skilled in the art readily appreciate that the conditions can change based upon the equipment used. Thus, those skilled in the art, as part of ordinary practice, and without undertaking undue experimentation, typically perform systematic studies whereby time, temperature, and sample size can be varied to determine how the pyrolysis conditions can be optimized.

In one or more exemplary embodiments, pyrolysis is conducted at a temperature of at least 500° C., in other embodiments at a temperature of at least 600° C., and in other embodiments at a temperature of at least 700° C. In these or other embodiments, pyrolysis is conducted at a temperature of at most 1000° C., in other embodiments at a temperature of at most 900° C., and in other embodiments at a temperature of at most 800° C. In one or more embodiments, pyrolysis is conducted at a temperature of from about 500° C. to about 1000° C., in other embodiments from about 600° C. to about 900° C., and in other embodiments from about 700° C. to about 800° C. For purposes of this specification, pyrolysis temperature refers to temperature of the device providing heat to the sample, not the temperature of the sample.

In one or more embodiments, pyrolysis is conducted for a time interval of at least 3 seconds, in other embodiments for a time interval of at least 5 seconds, and in other embodiments for a time interval of at least 7 seconds. In these or other embodiments, pyrolysis is conducted for a time interval of at most 20 seconds, in other embodiments for a time interval of at most 18 seconds, and in other embodiments for a time interval of at most 16 seconds. In one or more embodiments, pyrolysis is conducted for a time interval of from about 3 to about 20 seconds, in other embodiments for a time interval of from about 5 to about 18 seconds, and in other embodiments for a time interval of from about 7 to about 16 seconds. For purposes of this specification, pyrolysis time refers to time that the sample is subjected to the pyrolysis temperature.

In one or more embodiments, the sample size of the polymer sample that is pyrolyzed may be at least 0.5 mg, in other embodiments at least 0.7 mg, and in other embodiments at least 0.9 mg. In these or other embodiments, the size of the polymer sample that is pyrolyzed may be at most 1.5 mg, in other embodiments at most 1.3 mg, and in other embodiment at most 1.1 mg. In one or more embodiments, the size of the polymer sample that is pyrolyzed may be from about 0.5 to about 1.5 mg, in other embodiments from about 0.7 to about 1.3 mg, and in other embodiments from about 0.9 to about 1.1 mg. Those skilled in the art appreciate that manufacturer specifications for pyrolysis and/or GC equipment can provide useful guidance.

While combinations of sample size, pyrolysis temperature, and pyrolysis time may be chosen to achieve maximum trimer concentration, in an exemplary embodiment, pyrolysis of a 1 mg sample may take place at a temperature of 700° C. for 6 seconds.

Practice of the pyrolysis step of the present invention is not necessarily limited by the use of any particular equipment. Those skilled in the art will be able to readily select appropriate equipment to complete the step of pyrolyzing the polymer sample to form styrene monomer fragments, styrene dimer fragments, and styrene trimer fragments. In one or more embodiments, pyrolysis of the polymer sample may take place within a pyrolysis unit such as those sold under the tradename CDS for use in conjunction with a gas chromatograph. Other useful equipment includes those sold by Frontier.

Once the polymer sample has been fragmented, the fragments are analyzed to determine the relative amounts of the styrene monomer fragments, styrene dimer fragments, and styrene trimer fragments that are formed by the pyrolysis step. In one or more embodiments, analysis of the fragments includes separation of the fragments into groups and analysis of the groups to determine the relative quantities of fragments within the group.

In one or more embodiments, separation of the fragments into groups is carried out between a stationary phase and a gas mobile phase. As those skilled in the art will appreciate, this separation can be accomplished by using gas chromatography, which may also be referred to as gas-liquid partition chromatography (GLPC), which may also be referred to simply as gas chromatography (GC). In one or more embodiments, the GLPC techniques can be practiced by using a column such as an HP-5MS column (Agilent), which is believed to be a polysiloxane-based column having about 5% phenyl groups.

As those skilled in the art appreciate, the separation conditions, such as flow rate and temperature, can be manipulated to achieve different results. And, those skilled in the art readily appreciate that the conditions can change based upon the equipment used. Thus, those skilled in the art, as part of ordinary practice, and without undertaking undue experimentation, typically perform systematic studies whereby flow rate and temperature are varied to optimize separation conditions to achieve desired base-line separation.

In an exemplary embodiment, the temperature profile within the column may begin with an initial temperature of from about 30° C. to about 60° C., in other embodiments from about 35° C. to about 50° C., and in other embodiments from about 40° C. to about 45° C. In one or more embodiments, the temperature profile may include maintaining this initial temperature for a period from about 0.5 to about 4 minutes, in other embodiments from about 1 to about 3 minutes, or in other embodiments from about 1.5 to about 2.5 minutes.

In these or other embodiments, the temperature within the column can be increased at a rate of from about 10° C. to about 20° C. per minute, in other embodiments at a rate of from about 12° C. to about 18° C. per minute, and in other embodiments at a rate of from about 14° C. to about 16° C. per minute. And, for example, the temperature profile may end with a final temperature of from about 240° C. to about 280° C., in other embodiments from about 250° C. to about 270° C., or in other embodiments from about 255° C. to about 265° C.

Also, in exemplary embodiments, such as where a 30 meter column is employed, the flow rate through the column may be at least 0.5 mL/min, in other embodiments at least 1.0 mL/min, and in other embodiments at least 1.3 mL/min. In these or other embodiments, the flow rate through the column may be at most 10 mL/min, in other embodiments at most 7 mL/min, in other embodiments at most 5 mL/min, in other embodiments at most 4 mL/min, in other embodiments at most 3 mL/min, and in other embodiments at most 2 mL/min.

Once the fragments are separated into groups including styrene monomer groups, styrene dimer groups, and styrene trimer groups, the quantities of the fragments in the monomer group, dimer group, and trimer group are determined relative to one another. In other words, the data obtained relating to the quantity of the fragments is normalized to 100% to provide the relative percentages of the styrene monomer fragments, the styrene dimer fragments, and the styrene trimer fragments based on the total of the styrene monomer fragments, the styrene dimer fragments, and the styrene trimer fragments.

Practice of the present invention is not necessarily limited by the type of detection equipment or the technique employed. In one or more embodiments, a detector or technique that is capable of providing a response proportional to or representative of the quantity of the fragments in each target group is employed. In one or more embodiments, the quantities of the fragments in each group can be determined by flame ionization detection (FID). In other embodiments, the relative quantities of the fragments can be determined by thermal conductivity detection (TCD), in other embodiments it may be determined by mass spectrometry, such as by single-line monitoring of mass spectrometry. In one or more embodiments, the detection conditions are manipulated to maximize detection of the fragments having the smallest quantity, which in one or more embodiments is the styrene monomer fraction.

As those skilled in art appreciate, when using an FID, at least two preliminary steps must generally be taken. First, knowledge must be obtained on the retention time of the desired fragments. And, second, a peak must be chosen for the desired fragment in view of the fact that multiple peaks (which represent retention times) may exist for any given fragment, especially dimer and trimer fragments. Typically, those skilled in the art will rely on the peak with the most abundance, which is generally associated with the most thermally-stable fragment.

In one or more embodiments, a sample of the copolymer for which a microblock determination is sought is also subjected to analysis to determine the total styrene content of the copolymer. As discussed above, data relating to total styrene content can also be used to better analyze microblock content, but the data and/or the analysis is not required in practicing the present invention.

Practice of these embodiments of the present invention is not limited by the technique employed to determine total styrene content of the copolymer in question. In one or more embodiments, the total styrene content is determined by Fourier transform infrared spectroscopy (FTIR), which is a technique well known to those skilled in the art.

Other methods that can be employed to determine total styrene content of the copolymer sample include NMR.

As mentioned above, once data is obtained from a copolymer of unknown microblock content, the data (e.g., styrene monomer fragment content, styrene dimer frangment content, and styrene trimer fragment content) can be applied to a mathematical model to predict the styrene microblock content of the sample.

Mathematical Model

A mathematical model to which data from a copolymer sample is applied can be prepared by using techniques set forth herein. As discussed above, it has unexpectedly been discovered that a relationship exists between relative amounts of fragments resulting from pyrolysis of styrene-containing copolymers and the styrene microblock content of the copolymers. In particular embodiments, the relative styrene monomer fragment content (deriving from single styrene mer units within a copolymer), relative styrene dimer fragment content (deriving from two styrene mer repeat units within a copolymer), relative styrene trimer content fragment (deriving from three styrene mer repeat units within a copolymer), and the total microblock content of the copolymer provide a particularly advantageous relationship. And, it has been discovered that these relationships can be expressed mathematically to develop a mathematical model from which the microblock content of sample copolymers can be predicted, which for purposes of this specification may also be referred analyzed or determined. Thus, by determining, for example, the relative styrene monomer content, relative styrene dimer content, and relative styrene trimer content of a copolymer having a known microblock content (the latter being known, for example, from NMR analysis) a mathematical model can be prepared and used for subsequent predictions of microblock content of a copolymer sample with unknown microblock content.

In one or more embodiments, the relationship between the relative quantity of the styrene monomer fragments, the relative quantity of the styrene dimer fragments, the relative quantity of the styrene trimer fragments, and the microblock content of the copolymer, can be mathematically expressed by using a least square fitting method. Accordingly, a linear model can be developed from the relative quantity of the styrene monomer fragments, the relative quantity of the styrene dimer fragments, the relative quantity of the styrene trimer fragments, and the microblock content of a copolymer having known microblock content.

In one or more embodiments, the microblock content of a copolymer can be determined by known methods, such as NMR, and then the copolymer of known microblock content can be pyrolyzed into fragments and analyzed according to methods described herein to determine the relative quantities of styrene monomer fragments, the styrene dimer fragments, and styrene trimer fragments. From this data, a linear model can be formulated using known techniques for linear least square fitting.

For example, a linear model can have the formula:

$$\% \text{ Microblock} = \Sigma(\text{coefficient}) * (\text{response})$$

where the response represents the relative quantity of the fragment in question.

In one or more embodiments, the copolymers having known microblock content may be referred to as copolymer standards, e.g. poly(styrene-co-butadiene) standards. The number of standards that are analyzed according to methods described herein to determine monomer, dimer, and trimer fragments may vary based upon statistical preferences. In one or more embodiments, the number of copolymer standards analyzed in building the mathematical model may include at least 9 standards, in other embodiments at least 12 standards, and in other embodiments at least 15 standards. In these or other embodiments, and with the understanding that there need not necessarily be any cap to the number of copolymer standards analyzed in building the mathematical model, the number of copolymer standards may include at most 30 standards, in other embodiments at most 25 standards, in other embodiments at most 18 standards, and in other embodiments at most 16 standards.

In one or more embodiments, the copolymer standards may range in microblock content from about 10 to about 70 wt %, and in other embodiments from about 15 to about 60 wt % relative to the total styrene content. In one or more embodiments, the copolymer standards may include from about 10 to about 50 wt %, or in other embodiments from about 15 to about 45 wt %, or in other embodiments from about 20 to about 40 wt % total styrene based on the entire weight of the copolymer standard.

In one or more embodiments, an exemplary linear model having the following mathematical expression can be derived from the relative quantities of styrene monomer fragments (RMC), styrene dimer fragments (RDC), styrene trimer fragments (RTC), and known microblock content (MBC) of a collection of copolymer standards:

$$\% \text{ MBC} = (0.087 \times \text{RMC}) + (43.015 \times \text{RDC}) + (3.807 \times \text{RTC})$$

In one or more embodiments, data representing the total styrene content of the various copolymer samples within the collection of standards used to build the mathematical model is also determined and the data obtained from the analysis is incorporated into the mathematical model. An exemplary linear model having the following mathematical expression can be derived from the relative quantities of styrene monomer fragments (RMC), styrene dimer fragments (RDC), styrene trimer fragments (RTC), total styrene content (TS), and known microblock content (MBC) of a collection of copolymer standards:

$$\% \text{ MBC} = (0.0757 \times \text{RMC}) + (18.0077 \times \text{RDC}) + (12.2266 \times \text{RTC}) + (0.5097 \times \text{TS})$$

In one or more embodiments, other fragments can optionally be analyzed, and the data obtained can be included into the mathematical model with the relative monomer fragments, relative dimer fragments, and relative trimer fragments. For example, the relative amount of vinylcyclohexene can be determined and data relevant thereto can be incorporated into the formula; e.g.:

$$\% \text{ MBC} = (\text{coefficient} \times \text{RMC}) + (\text{coefficient} \times \text{RDC}) + (\text{coefficient} \times \text{RTC}) + (\text{coefficient} \times \text{TS}) + (\text{coefficient} \times \text{RVC})$$

where RMC is the relative quantity of styrene monomer fragments, RDC is the relative quantity of styrene dimer fragments, RTC is the relative quantity of styrene trimer fragments, TS is the total styrene content, and RVC is the relative quantity of vinylcyclohexene fragments. Without wishing to be bound by any particular theory, it is believed that the accuracy of the overall method can be increased by the inclusion of additional data relating to other fragments (e.g. vinylcyclohexene fragments). Those skilled in the art, however, will appreciate that reliance on data from those fragments that yield the greatest responses (which include monomer fragments, dimer fragments, and trimer fragments) will facilitate practice of the method of this invention.

Those skilled in the art, once armed with these or similar mathematical models, and the teachings provided herein, will be able to pyrolyze copolymer samples, analyze the samples to determine monomer, dimer, and trimer content (and optionally total styrene content) and use the data obtained to predict the microblock content of the copolymer sample. While this specification provides mathematical models and procedures that have proven to be technologically useful, those skilled in the art appreciate that the mathematical models may vary based upon the equipment used, as well as other conditions such as the preferences and/or bias of any given operator, and therefore it may be preferable to create a mathematical model using the same equipment and procedures that will ultimately be used to test copolymer samples.

In one or more embodiments, reference to styrene microblock content of the copolymer standards, which amount can be determined by known methods such as NMR, is a weight percentage of the styrene mer units that are located within styrene microblocks of the copolymer. Those skilled in the art appreciate that the term styrene microblocks can vary in terms of the number of repeat units of styrene mer units within a particular microblock. For example, those skilled in the art may define a microblock as including 3 to 10 mer units while other skilled artisans may define microblock to include 3 to 12 mer units. This lack of specificity, however, does not undermine an understanding or the ability to practice the present invention since the practice of the invention hinges on a mathematical model that is based upon known styrene microblock content. Thus, practice of this invention advantageously allows one to choose the meaning of microblock content based upon the meaning attributed to the known standards that are employed.

Industrial Applicability

Practice of the present invention provides a method by which styrene microblock content can be determined accurately and with quantitative precision without reliance on known methods such as NMR. This is advantageous for several reasons. For example, the methods described herein allow for the efficient determination of microblock content on-site where polymer is prepared such as a manufacturing facility or plant. These efficiencies allow for adjustments to the manufacturing process to tailor synthesis of the polymer and thereby achieve desired microblock content.

Accordingly, one or more embodiments of the present invention provide a method for producing a copolymer by polymerizing vinyl aromatic monomer and monomer copolymerizable therewith (e.g. conjugated diene monomer) under appropriate conditions and/or in the presence of a modifier that is capable of impacting the microblock content of the resulting copolymer. For example, styrene and 1,3-butadiene can be anionically polymerized in the presence of a modifier or randomizer (e.g., an ether, an ether-containing compound, a metal alkoxide, or an amine) to form a copolymer having polystyrene microblocks. In conjunction with the polymerization process, the analytical methods described herein can be practiced to provide information about the resulting copolymer and thereby allow adjustments to be made to the polymerization process to modify the polystyrene microblock content of subsequently synthesized copolymer. For example, the amount of and type of modifier employed can be adjusted, and/or the conditions of the polymerization, such as the temperature, percent conversion, the method of monomer addition, and/or combinations thereof with optional other parameters can be adjusted to manipulate the resulting micorblock content. In one or more embodiments, the analytical methods described herein are practiced at the same location (e.g. with the same plant or facility) in which the polymerization is conducted. This advantageously allows for the efficient and timely manipulation of the polymerization conditions to allow for adjustments to subsequent polymerizations in an effort to tailor desired polystyrene microblock content. In particular embodiments, the analytical techniques of this invention are conducted on-line within a continuous polymerization process. In other embodiments, the analytical techniques of this invention are conducted in conjunction with a batch or semi-batch process.

In order to demonstrate the practice of the present invention, the following examples have been prepared and tested. The examples should not, however, be viewed as limiting the scope of the invention. The claims will serve to define the invention.

EXAMPLES

Fifteen poly(styrene-co-butadiene) copolymers were prepared with varying total styrene content and varying styrene microblock content by using known techniques to vary the amount of styrene and the microblock content. These copolymers, which may also be referred to as copolymer standards, were analyzed by NMR to determine total styrene content (wt %) and microblock content (wt %) Unless otherwise stated, each sample was analyzed three times by NMR and the data reported is an average of the three results obtained; statistical analysis of the data showed at most 0.15% variation in the data obtained. Styrene microblock content was based upon blocks having 3 to 10 styrene units. As those skilled in the art understand, the total styrene content could have also been determined by FTIR. Table I below provides the data obtained from the NMR analysis.

TABLE I

| Sample name | % RMC | % RDC | % RTC | % Total Styrene | % MicroBlock Styrene |
|---|---|---|---|---|---|
| SBR-1 | 99.52 | 0.25 | 0.23 | 20.3 | 11.8 |
| SBR-2 | 97.96 | 0.60 | 1.43 | 26.7 | 37.5 |
| SBR-3 | 97.12 | 0.91 | 1.97 | 36.3 | 57.0 |
| SBR-4 | 96.85 | 0.88 | 2.27 | 36.1 | 52.9 |
| SBR-5 | 97.51 | 0.89 | 1.61 | 36.5 | 51.8 |
| SBR-6 | 97.63 | 0.90 | 1.48 | 35.7 | 46.5 |
| SBR-7 | 97.96 | 0.84 | 1.20 | 32.2 | 41.8 |
| SBR-8 | 97.59 | 1.07 | 1.34 | 40.7 | 50.2 |
| SBR-9 | 97.47 | 0.90 | 1.64 | 33.0 | 44.5 |
| SBR-10 | 98.06 | 0.70 | 1.24 | 32.9 | 40.1 |
| SBR-11 | 97.62 | 0.91 | 1.47 | 35.4 | 48.0 |
| SBR-12 | 97.89 | 0.84 | 1.29 | 27.0 | 36.7 |
| SBR-13 | 98.01 | 0.74 | 1.25 | 27.0 | 36.3 |
| SBR-14 | 98.52 | 0.69 | 0.80 | 36.2 | 39.2 |
| SBR-15 | 97.65 | 0.84 | 1.52 | 34.4 | 48.8 |

The microblock reported in Table I and throughout the experimental section is a weight percentage of styrene blocks having 3 to 10 repeat units relative to the total styrene in the copolymer.

The copolymer standards were then subjected to pyrolysis, separation, and further analysis to determine the relative amounts of styrene monomer fragments, styrene dimer fragments, and styrene trimer fragments resulting from pyrolysis. Specifically, the samples were subjected pyrolysis-GC-FID using a pyrolysis unit CDS 5250 in conjunction with a gas chromatograph Agilent 7890 system and an FID detector. Sample sizes of the copolymer standards were 1 mg, the pyrolyzer valve-oven temperature was 300° C., the pyrolysis temperature was 700° C., and the pyrolysis time was 6 seconds. The transfer line from the pyrolysis unit to the GC column was 300° C. and the GC injection port temperature was 280° C. The GC split ratio was 1:50, the column employed was an HP-5MS (30 m×0.25 mm×0.5 micrometer film) column. The GC column flow rate was 2 mL/min, the air flow to the detector was 300 mL/min, the $H_2$ flow to the detector was 30 mL/min, and the $N_2$ gas to the detector was 30 mL/min. The GC oven was set at an initial temperature of 40° C. and with a hold time of 1 minute. The temperature was ramped up to a final temperature of 260° C. at a rate of 15° C./minute and hold time of 10 minutes for a total time of 25.7 minutes. Using the FID, the relative amounts of styrene monomer fragments, styrene dimer fragments, and styrene trimer fragments were determined. Each sample was analyzed five times by pyrolysis-GC-FID and the data, which is reported in Table I, is an average of the five analyses; statistical analysis shows that the samples varied by less than 0.15%.

Based upon the data obtained, a linear design matrix was made where relative monomer content (RMC), relative dimer content (RDC), relative trimer content (RTC), and total styrene content (TS) were used as matrix X and microblock content (obtained from NMR described above) was used as matrix Y. Using linear least square fitting methods, the following equation was derived:

% Microblock Styrene=(0.0757×RMC)+(18.0077×RDC)+(12.2266×RTC)+(0.5097×TS)

Nine additional poly(styrene-co-butadiene) copolymers (referred to as Copolymers I-IX) were made and analyzed by NMR to determine the microblock content using procedures similar to those described above. The results of this analysis are provided in Table II below. Specifically, the nine additional copolymer samples were also pyrolyzed and analyzed by pyrolysis-GC-FID according to practice of the present invention to determine relative styrene monomer content, relative styrene dimer content, and relative styrene trimer content. FTIR analysis was used to determine the total styrene content. Using the data of relative styrene monomer content, relative styrene dimer content, relative styrene trimer content, and total styrene for each of the samples, together with the above equation, the microblock content of the nine polymer samples was predicted using techniques of this invention. Additionally, polystyrene microblock content was also determined by NMR. The data obtained from NMR and the techniques of this invention are provided in Table II. The data in Table II was plotted to give a linear cross-correlation of $R^2=0.9375$. In other words, the cross-correlation shows that the data obtained by practicing this invention is highly accurate and correlates with statistical significance to data obtained by NMR.

TABLE II

| Sample name | % Micro Block Styrene (Pyrolysis-GC-FID) | % MicroBlock Styrene (NMR) |
|---|---|---|
| SBR-16 | 45.5 | 49.5 |
| SBR-17 | 48.5 | 49.7 |
| SBR-18 | 44.7 | 49.2 |
| SBR-19 | 29.8 | 24.5 |
| SBR-20 | 46.9 | 48.9 |
| SBR-21 | 40.1 | 38.3 |
| SBR-22 | 47.7 | 51.7 |
| SBR-23 | 33.6 | 27.5 |
| SBR-24 | 37.2 | 39.5 |

Various modifications and alterations that do not depart from the scope and spirit of this invention will become apparent to those skilled in the art. This invention is not to be duly limited to the illustrative embodiments set forth herein.

What is claimed is:

1. A method for determining the styrene microblock content of a copolymer sample, the method comprising:
   (i) pyrolyzing the copolymer sample to form polymer fragments of the polymer sample;
   (ii) analyzing the fragments to determine the relative amounts of styrene monomer fragments, styrene dimer fragments, and styrene trimer fragments, where the relative amounts of the fragments include the amount of any given fragment relative to the total of the monomer fragments, dimer fragments, and trimer fragments; and
   (iii) using the relative amounts of the styrene monomer fragments, styrene dimer fragments, and styrene trimer fragments to predict the polystyrene microblock content from a mathematical model that is based upon the relative styrene monomer fragments, relative styrene dimer fragments, relative styrene trimer fragments, and microblock content of a copolymer having known microblock content.

2. The method of claim 1, where said step of pyrolyzing the polymer takes place at a temperature from about 500° C. to about 1000° C.

3. The method of claim 2, where said step of pyrolyzing the polymer takes place for a time interval from about 3 to about 20 seconds.

4. The method of claim 1, where said step of analyzing the fragments of the polymer includes separating the fragments into a styrene monomer fragments group, a styrene dimer fragments group, and a styrene trimer fragments group.

5. The method of claim 4, where said step of separating is carried out between a stationary phase and a gas mobile phase.

6. The method of claim 5, where said step of separating takes place within a gas chromatograph.

7. The method of claim 4, where said step of analyzing the fragments includes determining the quantity of the fragments within the styrene monomer fragments group, the styrene dimer fragments group, and the styrene trimer fragments group.

8. The method of claim 7, where said step of determining the quantity of the fragments within the styrene monomer fragments group, the styrene dimer fragments group, and the styrene trimer fragments group includes ionizing the fragments to produce ions and determining the quantity of these ions.

9. The method of claim 8, where said step of determining the quantity of the fragments within the styrene monomer fragments group, the styrene dimer fragments group, and the styrene trimer fragments group takes place within a flame ionization detector.

10. The method of claim 1, where said mathematical model is a design matrix developed from a linear least square fitting method using the relative styrene monomer fragments, relative styrene dimer fragments, relative styrene trimer fragments, and styrene microblock content of the copolymer having known styrene microblock content.

11. The method of claim 10, where the relative styrene monomer fragments, relative styrene dimer fragments, and relative styrene trimer fragments of the copolymer having known styrene microblock content is determined by (i) pyrolyzing the copolymer having known styrene microblock content to form fragments of the copolymer, and (ii) analyzing the fragments to determine the relative amounts of styrene monomer fragments, styrene dimer fragments, and styrene trimer fragments, where the relative amounts of the fragments include the amount of any given fragment relative to the total of the monomer fragments, dimmer fragments, and trimer fragments.

12. The method of claim 1, further comprising the step of determining the total styrene content of the copolymer sample, and using the relative amounts of the styrene monomer fragments, styrene dimer fragments, styrene trimer fragments, and total styrene content of the copolymer sample to predict the polystyrene microblock content from a mathematical model that is based upon the relative styrene monomer fragments, relative styrene dimer fragments, relative styrene trimer fragments, total styrene content, and microblock content of a copolymer having known microblock content.

13. A method for synthesizing a copolymer, the method comprising the steps of:
 (i) polymerizing vinyl aromatic monomer and conjugated diene monomer to form a copolymer;
 (ii) obtaining a sample of the copolymer prepared by said step of polymerizing;
 (iii) determining the polystyrene microblock content the sample by (a) pyrolyzing the copolymer sample to form polymer fragments of the polymer sample; (b) analyzing the fragments to determine the relative amounts of styrene monomer fragments, styrene dimer fragments, and styrene trimer fragments, where the relative amounts of the fragments include the amount of any given fragment relative to the total of the monomer fragments, dimer fragments, and trimer fragments; and (c) using the relative amounts of the styrene monomer fragments, styrene dimer fragments, and styrene trimer fragments to predict the polystyrene microblock content from a mathematical model that is based upon the relative styrene monomer fragments, relative styrene dimer fragments, relative styrene trimer fragments, and microblock content of a copolymer having known microblock content; and
 (iv) optionally adjusting said step of polymerizing to adjust the microblock content of the copolymer.

\* \* \* \* \*